(12) United States Patent
Saito et al.

(10) Patent No.: US 7,209,578 B2
(45) Date of Patent: Apr. 24, 2007

(54) IMAGE BASED MEDICAL REPORT SYSTEM ON A NETWORK

(75) Inventors: Motoaki Saito, San Mateo, CA (US); Kazuo Takahashi, San Mateo, CA (US)

(73) Assignee: TeraRecon, Inc., San Mateo, CA (US)

( * ) Notice: Subject to any disclaimer, the term of this patent is extended or adjusted under 35 U.S.C. 154(b) by 863 days.

(21) Appl. No.: 10/241,700

(22) Filed: Sep. 10, 2002

(65) Prior Publication Data
US 2003/0156745 A1    Aug. 21, 2003

(30) Foreign Application Priority Data
Sep. 11, 2001    (JP)    ............................. 2001-318705

(51) Int. Cl.
*G06K 9/00*    (2006.01)

(52) U.S. Cl. .................... 382/128; 382/100; 382/132

(58) Field of Classification Search ................ 382/232, 382/128, 100, 129, 132, 133; 707/10, 201, 707/2, 104.1, 3; 600/300; 704/260; 345/581, 345/589, 601
See application file for complete search history.

(56) References Cited

U.S. PATENT DOCUMENTS

| | | | |
|---|---|---|---|
| 6,216,104 B1 * | 4/2001 | Moshfeghi et al. | ......... 704/260 |
| 6,551,243 B2 * | 4/2003 | Bocionek et al. | ........... 600/300 |
| 6,574,629 B1 * | 6/2003 | Cooke et al. | ................. 707/10 |

| | | | |
|---|---|---|---|
| 2005/0254729 A1 | 11/2005 | Saito et al. | ................. 382/305 |

FOREIGN PATENT DOCUMENTS

| | | |
|---|---|---|
| JP | 2001-00017 | 11/2001 |
| JP | 2003-085284 | 3/2003 |
| JP | 2003-135427 | 5/2003 |
| JP | 2003-00025 | 7/2003 |
| JP | 2005-044321 | 2/2005 |

OTHER PUBLICATIONS

Meyer-Ebrecht, "The 'Filmless' Radiology Department—A Challenge for the Introduction of Image Processing into the Medical Routine Work?", IEEE, Apr. 1992, pp. 13-20.*

* cited by examiner

*Primary Examiner*—Anh Hong Do
(74) *Attorney, Agent, or Firm*—Blakely Sokoloff Taylor & Zafman, LLP

(57) ABSTRACT

A system to create and review reports enables interactive manipulation of the displaying of two-dimensional and three-dimensional images associated with image diagnosis reports, at user terminals connected to a medium- or low-speed network. High-speed image processing devices are set up near the network of a PACS server which archives and transmits medical image data, and parameter sets are attached which serve to recreate reference images in diagnosis reports. When users at a requesting department review the reports at user terminals, parameter sets are added to the reports and transmitted to image processing devices. The image processing devices obtain image data from the PACS server based on these parameter sets. Image processing is performed, and the image data is then sent to user terminals.

28 Claims, 4 Drawing Sheets

IMAGE BASED MEDICAL REPORT SYSTEM ON A NETWORK

FIELD OF THE INVENTION

This invention relates to a network-based system that uses medical image data and creates image reports corresponding to such data.

BACKGROUND

Medical images which are collected with medical image diagnosis devices, such as X-ray devices or X-ray computed tomography (CT) devices in image diagnosis departments of medical institutions, are used for an image diagnosis called reading projection. The result of this image diagnosis is described in an image diagnosis report and sent to departments that requested the result.

In the past, X-ray images picked up with X-ray devices on X-ray films were collected by medical image diagnosis devices equipped with the digital design such as X-ray CT devices or the like, and these collected medical images were also printed onto films and then observed. Digital data containing medical images have been most recently stored by servers in order to improve storage and distribution of medical images, so that the data signal can be distributed when it is required through a network to image displaying devices and broadcast in a picture archiving communication system (PACS) where the data can be observed.

The results of the reading projection performed with conventional medical image diagnosis devices are then copied by hand into a form of an image diagnosis report and distributed to departments that requested the results. Instead of writing the report by hand, the report can be also prepared by a word processor and then printed on paper. In such cases, the image information that forms the basis of the image diagnosis is written into a diagnosis report as a handwritten sketch called schema and then transmitted by a physician specializing in medical diagnosis to requesting departments.

Most recently, so called hospital information systems (HISs) have been used to transmit image diagnosis reports created with word processors or the like for storage and to requesting departments. In this case, image diagnosis reports which are preserved as electronic files prepared with a word processor or the like are either sent to a terminal computer at a requesting department or transmitted as electronic mail. In order to reduce the amount of data transmitted through the network in such cases, the size of images contained in image data creating the basis for image diagnosis is reduced, the image resolution capability is reduced, and the number of pages in a report is greatly reduced in pages attached to an image diagnosis report.

For example, although several hundred pages of 16-bit image data having 512×512 picture elements are generated with one scan of the latest X-ray CT scan, even in this case only about one to two pages will contain images having 256×256 picture elements and a depth of eight bits will be attached.

Moreover, when three-dimensional images are created with the latest X-ray CT scanning or MRI scanning technique, the performance of image diagnosis starts when this three-dimensional image is observed. Because the object of a three dimensional image is displayed stereoscopically, the direction of the line of sight can be changed interactively, and similar changes are possible to enable observation from multiple angles. This makes it possible to provide very beneficial information not only for image diagnosis purposes, but information that is beneficial also for other departments, for example, to create a plan for orthopedic surgery, etc. However, because the amount of data that must be transmitted through a network is thus greatly increased, it is difficult to reproduce three-dimensional images created at other departments, and because data containing images is attached to an image report only as one to two pages containing two-dimensional images picked up on the plane of three-dimensional images, the original three-dimensional data are not generated for requesting departments.

Thus, the reason why images that can be used at a requesting department are limited in this manner is that there is a narrow bandwidth of the network for the connection from the image diagnosis department to a requesting department, making it difficult if not impossible to supply sufficient image data to a requesting department. Generally speaking, because there will be many requesting departments in a hospital, the number of computer devices that are used at user terminals is very high. Consequently, it is often difficult to design a network that would offer a high speed for all user terminals of computer devices.

SUMMARY OF THE INVENTION

A medical information system comprises a picture archiving communication system (PACS) system, an image processing system, a report creation device, and multiple user terminal devices. The PACS system is to archive medical image data generated by a medical imaging device. The image processing system is coupled in proximity to the PACS system and is to process the medical image data and to specify image processing parameters sets associated with the medical image data. The report creation device is coupled to the image processing system and is to create medical reports. The medical reports have associated therewith images based on the medical image data. The user terminal devices are to receive the reports and are for use by multiple users to review the reports, including displaying and allowing user manipulation of two-dimensional and three-dimensional medical images associated with the reports, wherein the image processing parameter sets are attached to the received reports.

Other features of the present invention will be apparent from the accompanying drawings and from the detailed description which follows.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

The present invention provides a system to create and review reports, enabling manipulation in an interactive manner of displayed two-dimensional and three-dimensional images associated with image diagnosis reports, at user terminals which are connected to a medium- or low-speed network. High-speed image processing devices are set up in the vicinity of the network of a PACS server which archives and transmits medical image data, and parameter sets are attached which serve to recreate reference images in diagnosis reports created by physicians specializing in image diagnosis. When users at a requesting department review the reports at user terminals, parameter sets are added to the reports and transmitted to image processing devices. The image processing devices obtain image data from the PACS server based on these parameter sets. Image processing is performed, and the image data are sent to user terminals after the image processing has been finished. Consequently, displaying of two-dimensional and three-dimensional images associated with reports can be performed in an interactive manner at the computer devices of user terminals even if a medium- or low-speed network is used.

Figure 1:
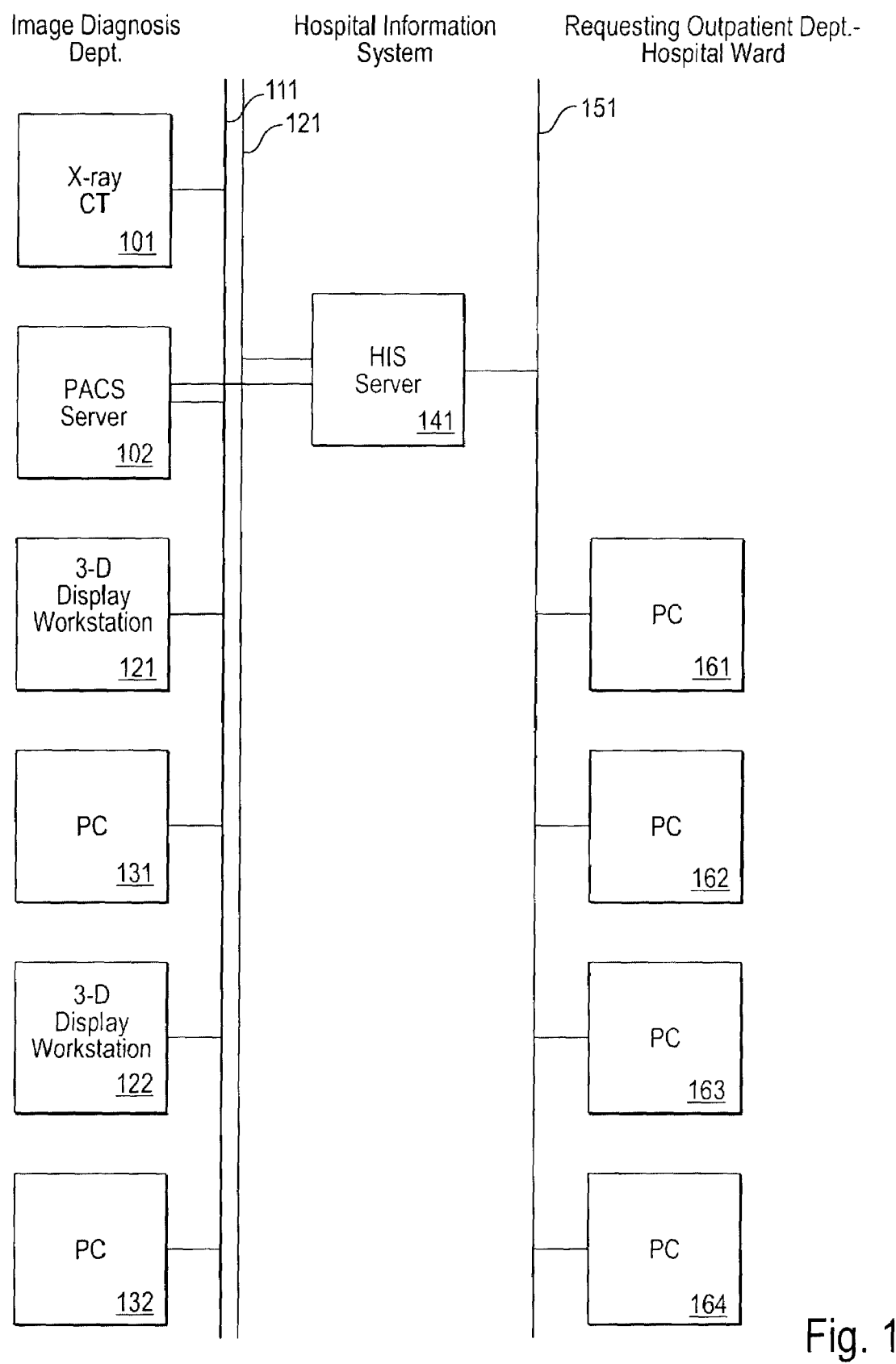
FIG. 1 is a construction block diagram of a conventional system for creating reports with medical images.

FIG. 1 is a block diagram showing a conventional network environment of image diagnosis devices of an image diagnosis department and requesting departments, and of the image display devices. X-ray CT device 101, which is one example of an image diagnosis device, creates image data collected as X-ray CT data of multiple detected objects having a plurality of profiles which are reconstructed. PACS server 102 is a server which stores image data that are collected and reconstructed with a plurality of image diagnosis devices, starting from the X-ray CT device 101 of a PACS that transmits the data to users as required. Image display workstations 121, 122, . . . are workstations used to create two-dimensional and three-dimensional images using these data, which are obtained via the network 111 as image data obtained from X-ray CT device 101 and archived by the PACS server 102. The network 111 is a large-capacity high-speed network transmitting to image display workstations large amounts of image data from the X-ray CT device 101 or PAC server 102. When an image diagnosis is performed during a medical image diagnosis, the image display workstations 121, 122, . . . are used, image data are collected from the X-ray CT device 101 or PACS sever 102 via the network 111. These data are processed by two-dimensional image processing and observed, and three-dimensional images are thus created and observed.

Personal computers 131, 132 are report-generating terminals used to create image diagnosis reports during an image medical diagnosis. Note that while only two personal computers 131, 132 are shown, essentially any number could be used. When an image medical diagnosis is performed during image diagnosis, image display workstations 121, 122 . . . are used for image processing and observation of two-dimensional images, and three-dimensional images are created and observed so that an image diagnosis report is created based on the findings obtained in this manner. At this point, the images creating the basis for the findings of image diagnosis information reports are attached to the image diagnosis information reports. As described above, because the network has a narrow bandwidth between the image diagnosis department and the requesting departments, approximately one to two pages of images with 256×256 picture elements and with a width of 8-bits are attached to an image diagnosis information report.

Even when an image is created and an image diagnosis has been performed, the image data that can be attached to an image report are attached as approximately one to two pages containing two-dimensional data picked up on the plane of three-dimensional images.

Hospital information system (HIS) server 141 stores images attached to the image diagnosis reports and distributes the image diagnosis reports with the attached images to the departments that have requested image diagnosis. HIS server 141 thus creates very large amounts of data containing images attached to image diagnosis reports that have been stored here, as the HIS server 141 manages the data for the entire hospital. This is also an important reason why the data amount of images attached to image diagnosis reports is limited.

Network 151 is a network used to distribute image diagnosis information stored on the HIS server 141 and images attached thereto to personal computers 161 through 164 of the user terminals at the requesting departments. Note that while only four personal computers 161, 162, . . . are shown, essentially any number could be used. Personal computers 161, 162, . . . of the user terminals at the requesting departments receive via the network 151 the image diagnosis reports stored in the HIS server 141 and the image information attached thereto. The users at the requesting departments use the computer devices 161, 162, . . . of the user terminals to review image diagnosis information and observe the images attached to it.

The images that are attached to the image diagnosis reports transmitted from the image diagnosis department to the requesting departments contain a relatively very limited amount of collected image data. Approximately one to two pages of images are attached to the image diagnosis reports, having 256×256 picture elements and a depth of 8 bits. In addition, even when three-dimensional images were created and image diagnosis was conducted, the image data that can be attached to the image reports is one to two pages of attached two-dimensional images picked up on the plane of a three-dimensional image. Also, at the requesting departments, many more two-dimensional images are observed in the same manner, and while there is a great need for the ability to manipulate three-dimensional images and for a better understanding of the images with a better depth of resolution, this has not previously been realized.

In order to achieve the above-mentioned task, a high-speed image processing server is deployed in the vicinity of a PACS server on a network. Image processing of two-dimensional image data is performed and image processing is performed also with the created three-dimensional images at this image processing server. Personal computers are used for processing of the images that are attached to the image diagnosis reports. Parameters required to create two-dimensional images and three-dimensional images are specified by the image processing server. Specified image data are read from the PACS server, and based on the specified image processing parameters, two-dimensional and three-dimensional image processing is performed. The resulting image data are transmitted to the personal computers of the user terminals. At the personal computers of the user terminals, the image data sent from the image processing server is displayed together with the image diagnosis reports, so that the image diagnosis reports can be understood. When required, the image processing parameters are modified in the personal computers at the user terminals. The modifications are sent to the image processing server. Image processing is then performed by the image processing server with these modified image processing parameters, and the result is sent to the personal computers at the user terminals.

Therefore, while previously it was possible to make available for requesting departments only one to two pages of images attached to an image diagnosis report, when image diagnosis reports are inspected at the requesting department according to this invention, the image processing parameters can be interactively modified based on the image processing parameter sets attached to image diagnosis reports. Because these are sent to an image processing server, and the results that have been processed by the image processing server are being sequentially received and displayed, it is possible to refer to different images that have been processed interactively to create different types of processed images, enabling a better depth of understanding of the content of image diagnosis reports.

For example, previously there were very few workstations capable of performing three-dimensional image processing, and since there were very few high-speed networks setup up at requesting departments, a long time was required in order to transmit image data over a network to a requesting department using three-dimensional processing from a PACS server. Also, because it was difficult for a physician to have the specialized know-how required in order to create three-dimensional images, three-dimensional images were used only at the image diagnosis department; they were seldom used at the requesting departments, where a very significant benefit could be expected from their utilization, for example, for orthopedic surgery. With this invention, an accelerated application of three-dimensional images can be expected.

Users at requesting departments transmit to the image processing server parameter sets for image processing of images attached to image diagnosis reports from the personal computers at the user terminals. For example, when a three-dimensional image of X-ray CT data is to be reviewed, X-ray CT data are specified to be used in order to create three-dimensional images with these image processing parameter sets, the parameters such as the spatial region for the object, the range of CT values and the like are specified, including projection processing parameters for display of three-dimensional images. Because when an image processing server creates three-dimensional images, the result is transmitted to personal computers, users at requesting departments can display the result images on the personal computers of the user terminals. While the images are being reviewed on the personal computers at user terminals, image processing parameters are interactively modified and when the images are transmitted to an image processing server, image processing is performed in accordance with image processing parameters that have been modified by an image processing server. Since the results are transmitted to user terminals, users at requesting departments can process images by using their personal computers as if they were working at a workstation that is used to process images.

Since image processing parameter sets include the stage wherein three-dimensional images are created by, for example, radiologists, consulting physicians in a requesting department can thus consult regenerated three-dimensional images created by specialists in the radiation department. This makes it possible to greatly improve the level of understanding on the part of the consulting physicians because the mutual understanding between the physicians who specialize in radiology and the consulting physicians in requesting departments is thus greatly improved when compared to the case when three-dimensional images created by radiology specialists were attached in one place to a written report and then sent to consulting physicians in requesting departments.

In the past, users used workstations connected to X-ray CT devices or a PACS system server for processing of three-dimensional images. In order to create a three-dimensional image, the used X-ray CT data were transmitted from an X-ray CT device or from a PACS server to a workstation used for processing of three-dimensional images. After parameters such as the CT range or the spatial region of an object were specified with a workstation and projection processing parameters were specified for three-dimensional display, three-dimensional images were created and the resulting image was displayed. In order to do that, workstations had to be set up for very expensive processing of three-dimensional images in each respective location where three-dimensional images were processed. In addition, in order to create a three-dimensional image, X-ray CT devices were required to produce a large amount of X-ray CT data, and also, PACS servers were required for transmission of images to workstations or for processing of three-dimensional images from a PACS server. Because a network having a high speed and a high capacity reaching up to the location of each individual user thus had to be set up to perform processing of three-dimensional images, this also greatly increased the traffic on the network.

Figure 2:
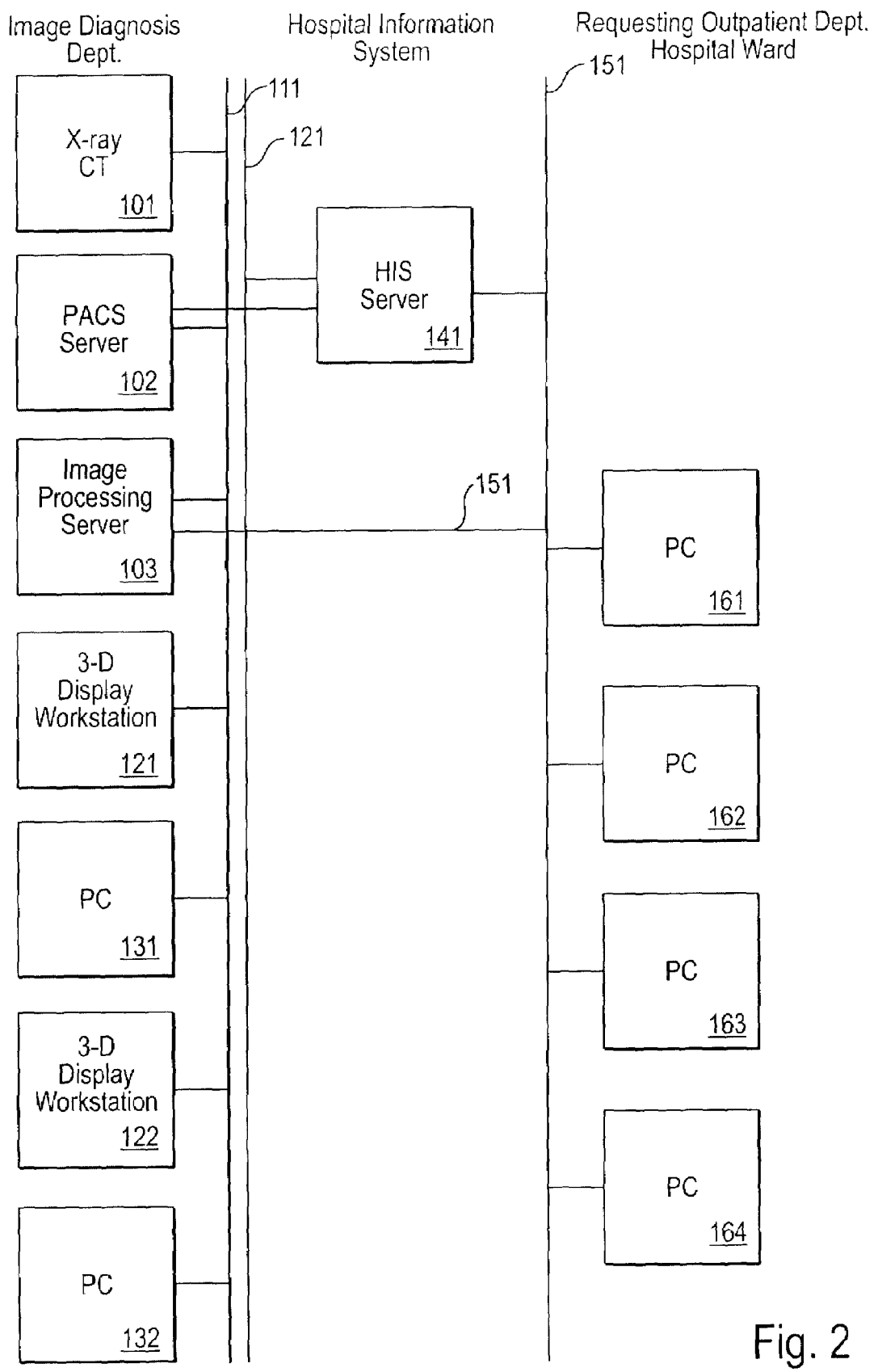
FIG. 2 is a construction diagram of a system utilizing medical image data and creating reports with medical images in a network environment according to a first embodiment of the invention.

FIG. 2 shows an embodiment of a system using medical image data creating medical image reports in a network environment, according to this invention. An X-ray CT device 101, which is one example of an image diagnosis device, collects X-ray CT data containing a plurality of profiles of a detected object. The data are reconfigured, and image data with a plurality of profiles are created. The data collected and reconfigured by a PACS server 102 in a plurality of image diagnosis devices, starting with X-ray CT device 101, are stored as image data and transmitted as required by the PACS server to users. Image display workstations 121, 122, . . . obtain image data stored by the X-ray CT device 101 or PACS server 102 via the network 111, and two-dimensional or three-dimensional images created by using this image data are displayed by image displaying workstations. The network 111 is a high-capacity and high-speed network transmitting from the X-ray CT device 101 or from the PACS server 102 a large amount of image data. Physicians performing image diagnosis use image display workstations 121, 122, . . . . Image data are obtained from the X-ray CT device 101 or from the PACS server 102 through the network 111, and using this data, two-dimensional images are processed and observed, and three-dimensional images are created and observed.

Personal computers 131, 132 . . . are terminals used to create reports that are created as image diagnosis reports by image diagnosis physicians. Image diagnosis physicians performing image diagnosis use image display workstations 121, 122, . . . for processing and observation of two-dimensional images and for processing and observation of three-dimensional images. At this point, images creating the basis for a finding in an image diagnosis report are created by using image processing parameter sets which are attached to image diagnosis reports. Because of that, parameters specifying key images are selected from a large amount of image data, including image processing parameters used to achieve optimal modes for display, or parameters required to create three-dimensional images.

An HIS server 141 stores sets of image processing parameters which are attached to the image diagnosis reports and distributes image processing parameter sets attached to the image diagnosis reports to requesting departments that have requested image diagnosis. A network 151 is used to distribute image diagnosis reports stored at the HIS server 141 with attached sets of image processing parameters to personal computers 161, 162, . . . of terminal users at the requesting departments.

Personal computers 161, 162, . . . of terminals of users in requesting departments receive, via the network 151, image processing parameter sets attached to the image diagnosis reports stored in the HIS server 141. The users at the requesting departments review image diagnosis reports by using personal computers terminal users 161, 162, . . . , and the image processing parameters attached to the reports are transmitted to the image processing server 103.

The image processing server 103 is a high-speed image processing server set up in the vicinity of a PACS server network. Accordingly, image processing of two-dimensional image data and image processing to create three-dimensional images are performed with the image processing server 103. The image processing server reads image data specified by the PACS server 102 based on the image processing parameters that are attached to the image diagnosis reports sent from personal computers 161, 162, . . . . Based on the image processing data parameters, two-dimensional and three-dimensional image processing is conducted, and the resulting image data are sent via the network 151 to the personal computers 161, 162, . . . .

At the personal computers 161, 162 . . . , images based on the image data transmitted from the image processing sever 103 are displayed together with the image diagnosis reports. The image processing parameters are then modified as required by the personal computers. The modified parameters are sent to the image processing server 103, and the image processing server 103 then performs image processing with these modified image processing parameters. The resulting image data are sent via network 151 to the personal computers 161, 162 . . . .

Because according to this invention, processing of two-dimensional and three-dimensional images requiring large amounts of image data is performed in a concentrated manner by the image processing server 103, and the resulting image data are distributed to personal computers 161, 162, . . . of the user terminals via the network 151, the traffic on the network 151 is thus not increased much.

The following types of parameters can be included in the image processing parameters that are attached to the reports:
1) patient specifying parameters,
2) image data specifying parameters,
3) parameters used to perform image processing,
4) parameters used to display images.

The foregoing explanation pertained to a case in which image processing parameter sets are used to create images creating the basis for a finding in an image diagnosis report. In another embodiment, however, identifiers are attached to image processing parameters of image diagnosis report, and image processing parameter sets corresponding to these identifiers are stored in a PACS server. In this case, the identifiers of image processing parameter sets are attached to image diagnosis reports. Identifiers of image processing parameter sets attached to image diagnosis reports are stored by the HIS server 141, and the image diagnosis is distributed to the requesting departments via the network 151, with the identifiers of image processing parameter sets attached to the image diagnosis reports.

Personal computers 161, 162, . . . at the requesting departments receive via the network 151 the identifiers of the image processing parameter sets attached to the image diagnosis reports stored at the HIS server 141. The image diagnosis reports are reviewed by the users of the personal computers, and the identifiers of the image processing parameter sets attached thereto are transmitted to the image processing server 103. When the image processing server 103 receives the identifiers of the image processing parameter sets, it will transmit these identifiers to the PACS server 102, and image processing parameters corresponding to these identifiers are obtained from the PACS server 102.

The image processing server 103 reads the image data specified by the PACS server 102 based on these image processing parameters, and based on the image processing parameters, processing of two-dimensional and three-dimensional images is performed and the resulting image data are transmitted to the personal computers 161, 162 . . . of the user terminals.

At the personal computers 162, 162 . . . , the image data sent from that image processing server 103 is displayed together with the image diagnosis report. If required, the personal computers 162, 162 . . . of the user terminals obtain from the server 103 image processing parameters used for image display, and parameters used to perform image processing from the image processing parameters. These parameters are modified and sent to the image processing server 103. The image processing server 103 performs image processing with these updated image processing parameters and the result is sent to the personal computers 162, 162 . . . of the user terminals. These operations can be performed repeatedly. In addition, updated parameters can be stored at the PACS server 102.

Figure 3:
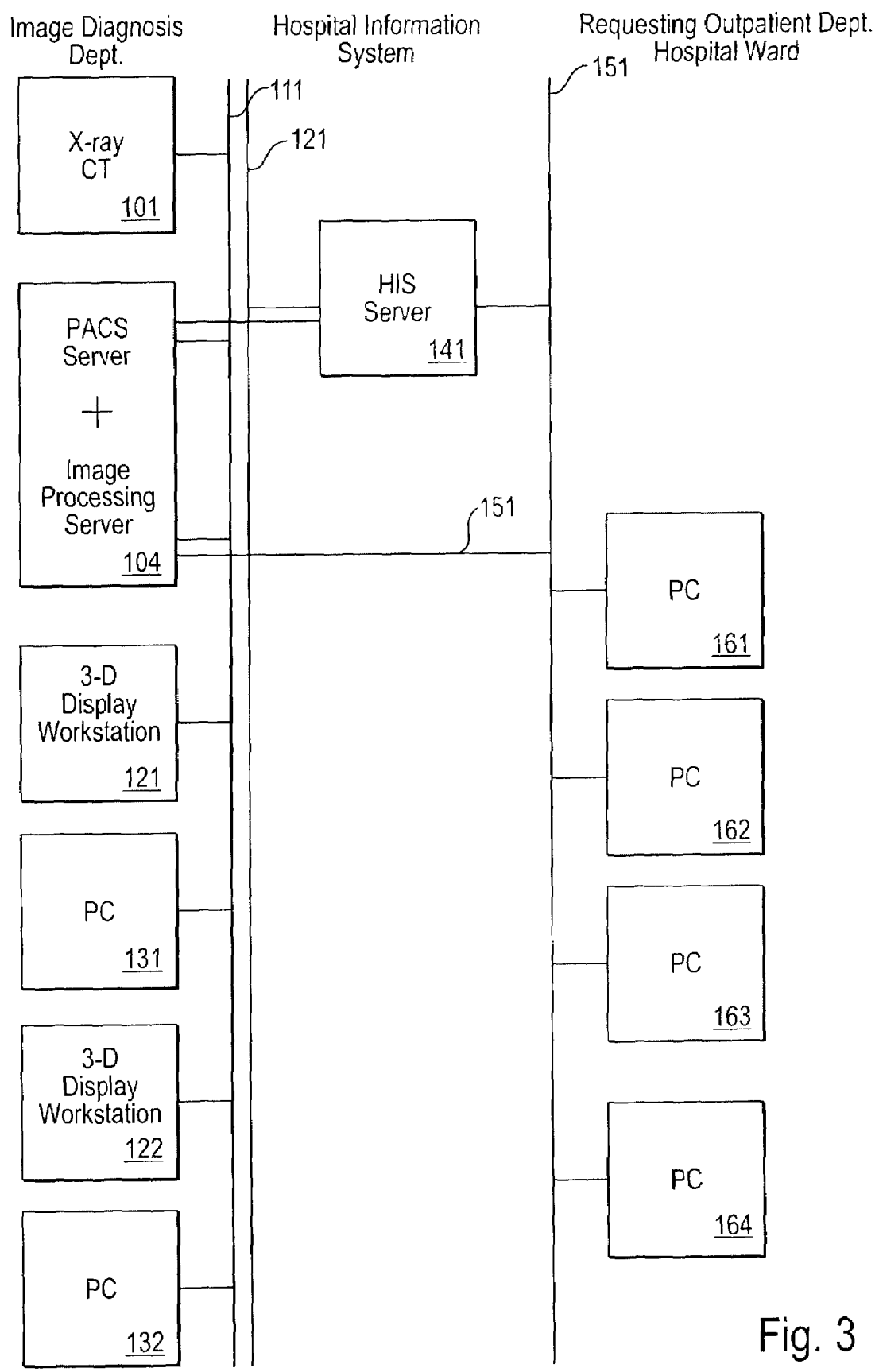
FIG. 3 is a construction diagram of a system utilizing medical image data and creating reports with medical images in a network environment according to a second embodiment of the invention.

FIG. 3 shows an embodiment of a configuration integrating a PACS server with an image processing server. The integrated PACS server-plus-image processing server 104 has a construction integrating the PACS server 102 with an image processing server 103. By integrating the construction of the PACS server with the image processing server, a close relationship is created between the data storage capability in a hospital and the image creating capability. This provides a high-speed design for acquisition of image data created with two-dimensional and three-dimensional images and reduces the load on the network.

Figure 4:
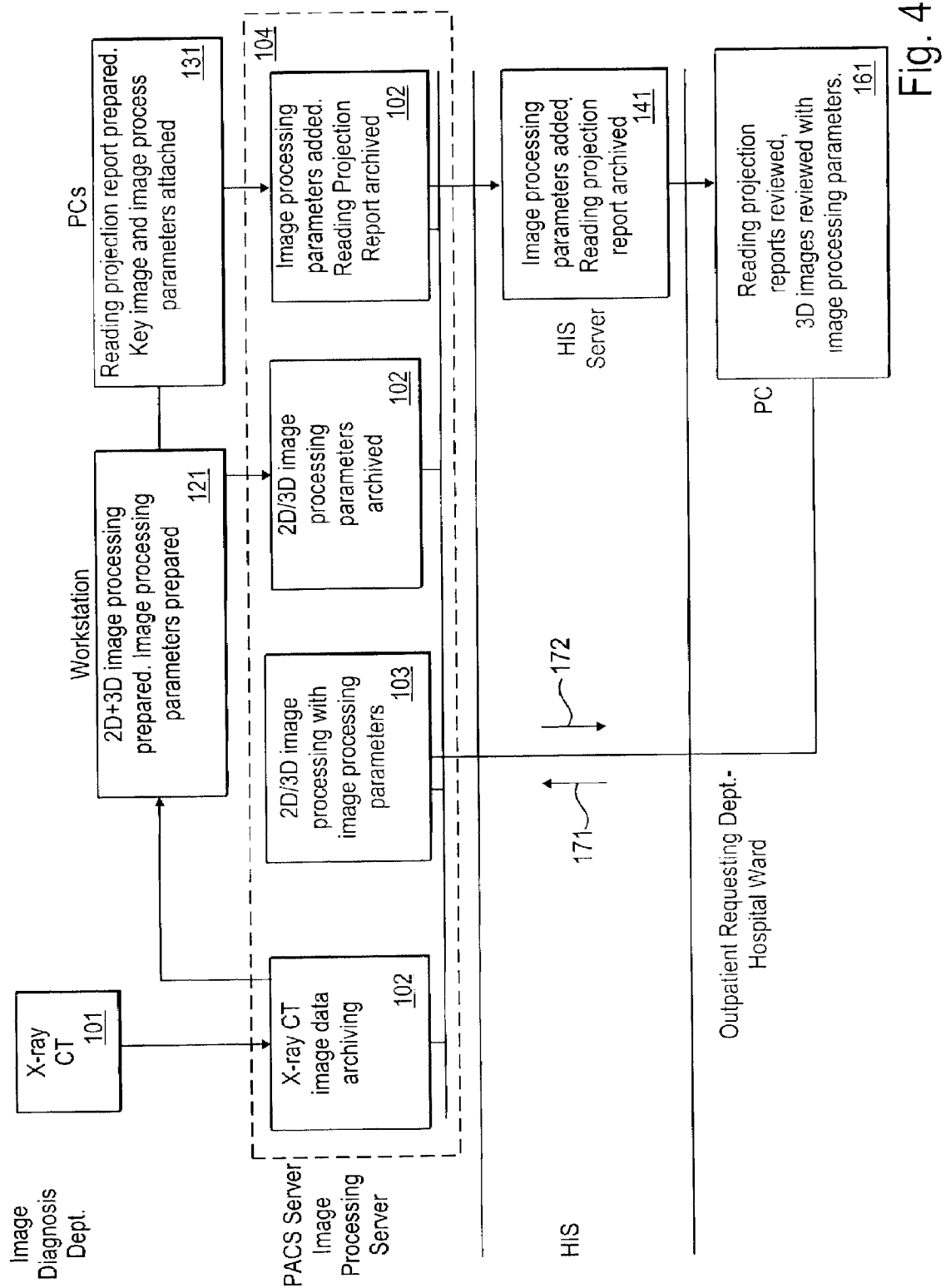
FIG. 4 is a block diagram of a system of the invention for using medical image data and for creating reports with medical images.

FIG. 4 shows a system and process of using medical image data and creating reports with medical images, in accordance with this invention. Image data created with an X-CT device 101 are sent to the PACS server 102 and stored therein. Image diagnosis department physicians process two-dimensional images and create three-dimensional images by using workstation 121 for image processing. Based on their findings, image diagnosis reports are created by using personal computers 131 for preparation of reports. Image processing parameters that are used during the processing of two-dimensional images and to create three-dimensional images are stored in the PACS server 102. In order to regenerate key images to help increase the level of understanding of the physicians at the requesting departments, the image processing parameters of the key images are attached to image diagnosis reports. The created image diagnosis reports and the image processing parameters attached thereto are stored at the HIS server 141 and sent via a network to the personal computers 161 of user terminals.

The physicians at the requesting departments use personal computer 161 of the user terminal to observe transmitted image diagnosis reports. By clicking on an icon of an image diagnosis report, image processing parameters 171 which are used to create key images are sent via a network to the image processing server 103. The image processing server 103 obtains from the PACS server 102 the required image data based on the transmitted image processing parameters. Based on the image processing parameters, two-dimensional and three-dimensional image processing of this image data is performed, and the resulting image 172 is sent to the personal computer 161.

Although physicians at the requesting department can observe this image as personal computer data at a user terminal, the image processing parameters can be modified and transmitted again to an image processing server. The image processing server 103 performs image processing based on the modified image parameters and sends the result to personal computers 161 of user terminals. These operations can be repeated interactively.

The foregoing pertained to an embodiment in which image profiles were created by using very powerful image processing workstations in an image diagnosis department. However, processing of medical image data can alternatively be performed with a high-speed image processing server, so that only reception and display of two-dimensional and three-dimensional images created by the image processing server that creates and transmits a control signal are performed with image displaying workstations. Personal computers having a low image processing capability which are also used as image display workstation can be used to perform image diagnosis. By doing so, the image display devices can be integrated with report-creating devices creating reports containing the results of image diagnoses based on the displayed images.

In yet another embodiment, the image processing server performs image data processing including compression at the time when a two-dimensional and three-dimensional image signal is received. In that case, because personal computers at the user terminals restore (decompress) two-dimensional and three-dimensional data when compressed image data are received, two-dimensional and three-dimensional images can be displayed and manipulated on personal computers of user terminals with an interactive response even if a medium- or low-speed network is used to connect the personal computers of user terminals with the image processing server.

In still another embodiment, image processing sets are created in order to create an image having a thumbnail image that is pasted into a report, or links are created for identifiers of image processing sets, so that by clicking on the thumbnail image, the parameter sets for image processing or the identifiers of the image processing parameter sets required to create an image are transmitted to an image processing server.

In still another embodiment, a controller is deployed for interactive updating of image processing parameters and of regions displaying images, which can be sent from an image processing server for image diagnosis reports that can be displayed on the screen of a user terminal. This makes it possible to use the embodiment even if specialized software has not been installed.

In yet another embodiment, images sent from an image processing device are displayed in a separate window provided for reports with this capability.

In still another embodiment, a user interface is displayed on the screen by clicking on a thumbnail image pasted in an image diagnosis report for updating of image parameters. This capability makes it possible to transmit image processing parameters that have been updated with these operations to an image processing server.

In a further embodiment, a user interface for updating of image processing parameters is displayed in a window that is separate from the report by clicking on a thumbnail image that is pasted into a report. This capability makes it possible to transmit image processing parameters that have been updated with these operations to an image processing devices.

Although the foregoing explanation was given in the context of X-ray CT devices and image data obtained from X-ray CT devices, the invention is also applicable to, for example, magnetic resonance (MR) devices, nuclear medicine devices, devices using ultrasonic waves and other medical imaging devices and image data obtained with such devices. In addition, the same capabilities are available also in cases when these medical devices and image data obtained form such devices are used simultaneously.

Thus, the invention makes it possible to use a low-speed network as a network connecting requesting departments. In addition, it is also possible to combine a network with another HIS without a specialized image network. Although in the image diagnosis department, it may be necessary in some cases to install a high-speed network between an image processing server and X-ray CT devices or a PACS server, a low-speed network can still be used between an image processing server and personal computers. Thus, the invention thus makes it possible to display and manipulate two-dimensional and three-dimensional images associated with reports at the user terminals in a realistic interactive manner, even if a medium- or low-speed network is used as a network connecting image processing devices with user terminals at requesting devices.

Multiple users can use one three-dimensional image processing system jointly with physicians specializing in image diagnosis. The specialized physicians perform specification of X-ray CT data used to create three-dimensional images, specification of parameters such as empty regions in objects, CT value ranges or the like, and specification of pick-up processing parameters for displaying of three-dimensional images. Because an image processing server transmits the resulting three-dimensional images thus created to a plurality of personal computers, one three-dimensional image processing system can be used jointly by a plurality of users. For example, the process wherein three-dimensional images were created and used by specialists who read the images in the radiology department can be recreated by consulting physicians in requesting departments who can thus observe these images.

The invention makes it possible to reduce the cost of the equipment as well as to reduce the space occupied by it. The equipment cost can be greatly reduced when a plurality of personal computers is used together with a high-speed image processing server instead of using a plurality of three-dimensional image processing workstations. In addition, using personal computers instead of workstations also makes it possible to reduce the occupied space.

Thus, described above is a system to create and review reports, enabling manipulation in an interactive manner of displayed two-dimensional and three-dimensional images associated with image diagnosis reports, at user terminals which are connected to a medium- or low-speed network. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A medical information system comprising:
a picture archiving communication system (PACS) to archive medical image data generated by a medical imaging device;
an image processing system coupled in proximity to the PACS to process the medical image data and to specify image processing parameter sets associated with the medical image data;
a report creation device coupled to the image processing system to create medical reports, the medical reports having associated therewith images based on the medical image data; and
a plurality of user terminal devices to receive the reports and for use by a plurality of users to review the reports, including displaying and allowing user manipulation of two-dimensional and three-dimensional medical images associated with the reports, wherein the image processing parameter sets are attached to the received reports, and wherein in response to receiving, from a user terminal device of the plurality of user terminal devices via a first network, updated image processing parameters associated with a report as a result of user manipulation of a displayed medical image, the image processing system processes the medical image data based on the updated image processing parameters to create updated medical images and transmits the updated medical images to the user terminal device, so as to enable interactive display and manipulation of medical images from the user terminal device.

2. A system as recited in claim 1, further comprising a hospital information system (HIS) server to archive the reports and to transmit the reports to the user terminal devices in response to requests.

3. A system as recited in claim 1, wherein the image processing system, the PACS and the report-creation device are coupled on a second network.

4. A system as recited in claim 3, wherein the plurality of user terminal devices are coupled on the first network, and wherein the image processing system is further coupled to the first network.

5. A system as recited in claim 4, further comprising a hospital information system (HIS) server, coupled to the first network and the second network, to archive the reports and to transmit the reports to the user terminal devices in response to requests.

6. The system of claim 1, wherein:
the PACS archives image processing parameter sets, associated with which are corresponding identifiers;
a user terminal device of the plurality of user terminal devices transmits to the image processing system the identifiers of said image processing parameter sets; and
the image processing system obtains image data from the PACS based on the image processing parameter sets corresponding to the identifiers and uses the obtained image data to process images.

7. The system of claim 1, wherein the PACS and the image processing system are integrated in a single device.

8. The system of claim 1 wherein the image processing system creates and transmits two-dimensional and three-dimensional image signals and a control signal to the user terminal devices, and the user terminal devices display medical images in response thereto.

9. The system of claim 1, wherein the report creation device is integrated with an image display device.

10. The system of claim 1, wherein the image processing system compresses the image data prior to transmitting the image data to the user terminal devices, and wherein the user terminal devices receive and decompress the compressed image data.

11. The system of claim 1, wherein one or more thumbnail images based on said medical image data are incorporated into the reports and are associated with said image processing parameter sets, and wherein, in response to a user input directed to one of the thumbnail images, corresponding image processing parameter sets or identifiers thereof are transmitted to the image processing system.

12. The system of claim 11, wherein each of the user terminal devices can display, in reports, images transmitted from the image processing system.

13. The system of claim 11, wherein each of the user terminal devices can display images transmitted from the image processing system in a window that is separate from an associated report.

14. The system of claim 11, wherein, in response to a user input directed to a thumbnail image attached to a report, image processing parameters are updated and transmitted to the image processing system.

15. The system of claim 11, wherein each of the user terminal devices can display, in a window that is separate from a report, a user interface to update image processing parameters in response to a user input directed to a thumbnail image incorporated into the report; wherein the updated image processing parameters are transmitted to the image processing system.

16. An information system to create and review reports associated with medical image data, the information system comprising:
a picture archiving communication system (PACS) server to archive medical image data generated by a medical imaging device;
an image processing server coupled to the PACS server on a first data network and further coupled to a second data network, the image processing server to process the medical image data and to specify image processing parameter sets associated with the medical image data;
a plurality of report creation devices coupled to the first data network to create reports containing the results of diagnoses based on medical images resulting from the medical image data;
a plurality of user terminal devices coupled to each other and to the image processing server on the second data network, to receive the reports and for use by a plurality of users to review the reports, including displaying and allowing user manipulation of two-dimensional and three-dimensional medical images associated with the reports, wherein the image processing parameter sets are attached to the received reports, and wherein in response to receiving, from a user terminal device of the plurality of user terminal devices via the second data network, updated image processing parameters associated with a report as a result of user manipulation of a displayed medical image, the image processing server processes the medical image data based on the updated image processing parameters to create updated medical images and transmits the updated medical images to the user terminal device, so as to enable interactive display and manipulation of medical images from the user terminal device; and
a hospital information system (HIS) server, coupled to the first data network and the second data network, to archive the reports and to transmit the reports to the user terminal devices in response to requests.

17. The system of claim 16, wherein:
- the PACS server archives image processing parameter sets, associated with which are corresponding identifiers;
- a user terminal device of the plurality of user terminal devices transmits to the image processing server the identifiers of said image processing parameter sets; and
- the image processing server obtains image data from the PACS server based on the image processing parameter sets corresponding to the identifiers and uses the obtained image data to process images.

18. The system of claim 16, wherein the PACS server and the image processing server are integrated in a single device.

19. The system of claim 16, wherein the image processing server creates and transmits two-dimensional and three-dimensional image signals and a control signal to the user terminal devices, and the user terminal devices display medical images in response thereto.

20. The system of claim 16, wherein the report creation devices are integrated with image display devices.

21. The system of claim 16, wherein the image processing server compresses the image data prior to transmitting the image data to the user terminal devices, and wherein the user terminal devices receive and decompress the compressed image data.

22. The system of claim 16, wherein one or more thumbnail images based on said medical image data are incorporated into the reports and are associated with said image processing parameter sets, and wherein, in response to a user input directed to one of the thumbnail images, corresponding image processing parameter sets or identifiers thereof are transmitted to the image processing server.

23. The system of claim 22, wherein each of the user terminal devices can display, in reports, images transmitted from the image processing server.

24. The system of claim 22, wherein each of the user terminal devices can display images transmitted from the image processing server in a window that is separate from an associated report.

25. The system of claim 22, wherein, in response to a user input directed to a thumbnail image attached to a report, image processing parameters are updated and transmitted to the image processing server.

26. The system of claim 22, wherein each of the user terminal devices can display, in a window that is separate from a report, a user interface to update image processing parameters in response to a user input directed to a thumbnail image incorporated into the report; wherein the updated image processing parameters are transmitted to the image processing server.

27. A method comprising:
- delivering a medical report document to a processing system of a recipient over a data network, the medical report document having a set of image parameters attached thereto;
- receiving, from the processing system of the recipient over the data network, a modified set of image parameters in response to a user input directed to a medical image displayed on the processing system, the medical image associated with the set of image parameters;
- in response to the user input, accessing medical image data from a server coupled to the data network;
- generating modified image data based on the modified set of image parameters and the accessed medical image data; and
- delivering the modified image data to the processing system of the recipient over the data network, such that the medical image displayed on the processing system of the recipient is modified interactively according to the user input.

28. A medical information system comprising:
- a picture archiving communication system (PACS) to archive medical image data generated by a medical imaging device;
- an image processing system coupled in proximity to the PACS to process the medical image data and to specify image processing parameter sets associated with the medical image data;
- a report creation device coupled to the image processing system to create medical reports, the medical reports having associated therewith images based on the medical image data, wherein in response to receiving, from a user terminal device via a data network, updated image processing parameters associated with a report as a result of user manipulation of a displayed medical image, the image processing system processes the medical image data based on the updated image processing parameters to create updated medical images and transmits the updated medical images to the user terminal device, so as to enable interactive display and manipulation of medical images from the user terminal devices.

* * * * *